United States Patent
Anderson et al.

(10) Patent No.: US 9,445,848 B2
(45) Date of Patent: Sep. 20, 2016

(54) SURGICAL IMPLANTS FOR PERCUTANEOUS LENGTHENING OF SPINAL PEDICLES TO CORRECT SPINAL STENOSIS

(71) Applicant: Innovative Surgical Designs, Inc., Bloomington, IN (US)

(72) Inventors: D. Greg Anderson, Moorestown, NJ (US); Wayne Beams, Bloomington, IN (US); Barry Turner, Columbus, IN (US); Ed Morris, Bloomington, IN (US)

(73) Assignee: Innovative Surgical Designs, Inc., Bloomington, IN (US)

( * ) Notice: Subject to any disclaimer, the term of this patent is extended or adjusted under 35 U.S.C. 154(b) by 0 days.

(21) Appl. No.: 13/656,192

(22) Filed: Oct. 19, 2012

(65) Prior Publication Data

US 2013/0123847 A1    May 16, 2013

Related U.S. Application Data

(60) Provisional application No. 61/549,848, filed on Oct. 21, 2011.

(51) Int. Cl.
    *A61B 17/70* (2006.01)
(52) U.S. Cl.
    CPC .................................. *A61B 17/7071* (2013.01)
(58) Field of Classification Search
    CPC .......... A61B 17/7059; A61B 17/7071; A61B 17/70; A61B 17/863; A61B 17/8685; A61B 17/68; A61B 17/7001; A61B 17/7032–17/7046; A61B 17/8625–17/866
    USPC .......................... 606/246, 90, 105, 300–321
    See application file for complete search history.

(56) References Cited

U.S. PATENT DOCUMENTS

| | | | |
|---|---|---|---|
| 6,869,432 B2 | 3/2005 | Schlapfer et al. | |
| 7,384,209 B2 * | 6/2008 | Muders et al. | 403/115 |
| 2003/0004517 A1 | 1/2003 | Anderson | |
| 2003/0212400 A1 | 11/2003 | Bloemer et al. | |
| 2005/0038438 A1 * | 2/2005 | Anderson et al. | 606/73 |

(Continued)

FOREIGN PATENT DOCUMENTS

| | | |
|---|---|---|
| CN | 101695453 | 4/2010 |
| WO | 2004047689 | 6/2004 |

OTHER PUBLICATIONS

Extended European Search Report and Opinion dated Oct. 16, 2015; issued in corresponding European Application No. 12841699.7; 7 pages.

(Continued)

*Primary Examiner* — Jacqueline Johanas
*Assistant Examiner* — Tessa Matthews
(74) *Attorney, Agent, or Firm* — Blank Rome LLP

(57) ABSTRACT

An implant to separate a vertebral cut has an upper portion, lower portion, and inner member. The inner member communicates with a swivelable coupling located at each end of the inner member. Each swivelable coupling also interacts with a respective one of the upper and lower portion, within an inner bore thereof. Movement of the inner member relative to one or both of the upper and the lower portions, via one or both swivelable couplings, translates the upper portion away from the lower portion, about a vertebral cut, to widen the vertebral cut and expand the spinal canal. Swivelable action of the couplings allows angulation of the inner member, relative to a longitudinal axis of the implant, to accommodate a natural lateral shift occurring during a widening of a vertebral cut.

20 Claims, 9 Drawing Sheets

(56) References Cited

U.S. PATENT DOCUMENTS

| | | | |
|---|---|---|---|
| 2006/0271054 A1* | 11/2006 | Sucec et al. | 606/73 |
| 2007/0168036 A1* | 7/2007 | Ainsworth et al. | 623/17.13 |
| 2007/0233062 A1 | 10/2007 | Berry | |
| 2008/0114403 A1 | 5/2008 | Kuester et al. | |
| 2008/0188895 A1* | 8/2008 | Cragg et al. | 606/246 |
| 2010/0036436 A1* | 2/2010 | Winslow et al. | 606/305 |
| 2010/0168751 A1* | 7/2010 | Anderson et al. | 606/82 |
| 2011/0152933 A1* | 6/2011 | Culbert et al. | 606/246 |
| 2011/0282387 A1* | 11/2011 | Suh et al. | 606/246 |

OTHER PUBLICATIONS

International Search Report dated Mar. 29, 2013; International Application No. PCT/US2012/061084; International Filing Date: Oct. 19, 2012; 6 pages.

Written Opinion dated Mar. 29, 2013; International Application No. PCT/US2012/061084; International Filing Date: Oct. 19, 2012; 4 pages.

International Preliminary Report on Patentability dated Apr. 22, 2014; International Application No. PCT/US2012061084; International Filing Date: Oct. 19, 2012; 5 pages.

China Office Action dated Jun. 25, 2015; in corresponding Chinese Application No. 201280057744.6; 13 pages.

English translation of China Office Action dated Jul. 8, 2015; in corresponding Chinese Application No. 201280057744.6; 4 pages.

English translation of China Application No. CN101695453 dated Oct. 1, 2015; 4 pages.

* cited by examiner

SURGICAL IMPLANTS FOR PERCUTANEOUS LENGTHENING OF SPINAL PEDICLES TO CORRECT SPINAL STENOSIS

RELATED INVENTIONS

This application claims benefit of priority of U.S. Provisional Application No. 61/549,848, entitled "Surgical Implants for the Percutaneous Lengthening of the Spinal Pedicles to Correct Spinal Stenosis," filed Oct. 21, 2011; which application is incorporated herein by reference.

FIELD OF THE INVENTION

The present invention relates generally to the field of corrective spinal procedures; and more particularly to a technique and apparatus for expanding a spinal canal by percutaneous cutting of the spinal pedicles and implantation of a novel device capable of lengthening and fixating the pedicles in expanded position.

BACKGROUND OF THE INVENTION

Spinal stenosis, or narrowing of the spinal canal, affects millions of people, leading to disabling back and leg pain due to compression of the spinal nerves. Patients with severe spinal stenosis often require major surgery involving a spinal laminectomy, wherein portions of the lamina, spinous process and facet joints are removed to reduce the compression of the spinal nerves. Although spinal laminectomy can successfully relieve pressure from the spinal nerves, it requires a major surgery and may lead to a variety of complications including spinal instability, excessive blood loss, medical complications, recurrent stenosis and nerve scarring. These potential problems reduce the desirability of spinal laminectomy and make this operation unsuitable for some elderly patients with significant, pre-existing medical problems.

Correction of spinal stenosis through lengthening of the spinal pedicles has recently been described (U.S. Pat. Nos. 8,157,847, 7,166,107 and 6,358,254) and involves a novel surgical procedure of cutting and lengthening the spinal pedicles using an implanted medical device which is able to enlarge the spinal canal and alleviate the symptoms of spinal stenosis. Pedicle lengthening is much less invasive compared to spinal laminectomy and is capable of achieving a permanent expansion of the spinal canal. However, because the anatomy of the spinal pedicles varies throughout the lumbar spine and also between individuals, it would be desirable to have an implant capable of adapting to these anatomic variations. In particular, in situations where the vertebrae with a high convergence angle of the pedicle, such as is often seen at the L5 level, pedicle lengthening produces an offset or lateral shift between the upper and lower bone segment at the site of the pedicle osteotomy (bone cut).

For the foregoing reasons, there is a need for an improved device to accommodate the variations that may be encountered in pedicle anatomy and to allow offset between the upper and lower bone segments at the site of the pedicle osteotomy.

SUMMARY OF THE INVENTION

The present invention provides several novel devices allowing improved accommodation of the variations in pedicle anatomy and allowing for the offset between the upper and lower bone segments of a vertebra occurring at the site of a pedicle osteotomy. The devices of the present invention are particularly pertinent when a subject pedicle has high convergence angle. The various embodiments disclosed herein involve a series of implantable devices having an upper and a lower portion bridged by a longitudinal (inner) member. All embodiments provide for neutralization of medially directed force vectors, and enhancement of anteriorly directed force vector, during a pedicle lengthening process.

Embodiments of the present invention will be seen variously:
  to provide a simple and safe methods and implants for performing percutaneous pedicle lengthening, ideal for accommodating variations in vertebral anatomy; and in particular for achieving pedicle lengthening in situations having high convergence angle between the pedicles;
  to allow optimal lengthening of the pedicles in vertebrae with high convergence angles between the pedicles;
  to enhance the work flow and efficiency of the percutaneous pedicle lengthening procedure;
  to improve the biomechanical strength of the fixation of the pedicle lengthening device; and
  to neutralize the medially directed force vectors produced by pedicle lengthening when there is convergence between the pedicles.

In one aspect of the invention, an implant for expanding a spinal canal is provided that includes an upper portion and a lower portion, each having an inner bore. The inner member is configured to communicate with a swivelable coupling at each end thereof. Each swivelable coupling can interact with a respective upper or lower portion, within the inner bore thereof. Movement of the inner member relative to one or both of the upper and the lower portions, via one or both swivelable couplings, translates the upper portion away from the lower portion, about a vertebral cut, to widen the vertebral cut, and expand the spinal canal. The swivelable action of the couplings during translation allows angulation of the inner member, relative to a longitudinal axis of the implant, to accommodate a change in shape of a vertebra during vertebral cut widening.

The inner bore of each of the upper and the lower portions could be conically shaped to accommodate angulation of the inner member during translation. Inner member angulation compensates for a lateral shift of the upper portion relative to the lower portion during translation.

In another aspect, one swivelable coupling can be swivelably fixed within one of the upper and the lower portions and the other coupling can be translatably and swivelably retained within the other of the upper and the lower portions. In this instance, the couplings can be permanently attached to respective ends of the inner member. Here, the swivelably fixed coupling can reside within an inner bore of one of the upper and the lower portions. A retaining ring can be placed within the respective inner bore to secure the coupling therein, but to continue to allow swivelable action of the coupling.

This aspect could have the translatably and swivelably retained coupling move longitudinally relative to one of the upper and the lower portions to translate the upper portion away from the lower portion, about the vertebral cut, to widen the vertebral cut and expand the spinal canal. In this aspect, the translatably and swivelably retained coupling can be housed within a widened inner bore of the upper portion, with the longitudinal movement thereof occurring from a proximal end of the widened inner bore to and finally against a distal end of the widened inner bore.

A retaining lock nut could be additionally included. The retaining lock nut could threadably engage inner walls of the widened inner bore of the upper portion, to advance and longitudinally move the translatably and swivelably retained coupling within the widened inner bore and to finally secure the translatably and swivelably retained coupling against the distal end of the widened inner bore to secure the upper portion relative to the lower portion, after translation, and to secure and maintain a width of the widened vertebral cut.

In a further aspect, the swivelable couplings are each swivelably fixed within a respective one of the upper and the lower portions, where one swivelably fixed coupling is permanently attached to one end of the inner member and the other swivelably fixed coupling has an internal passage therethrough. In this instance, movement of the inner member relative to and within the internal passage of the other swivelably fixed coupling translates the upper portion away from the lower portion. In this aspect, the internal passage of the other swivelably fixed coupling could be threaded and could engage exterior threads of the inner member to facilitate movement of the inner member relative thereto to translate the upper portion away from the lower portion.

A lock nut could additionally be included, the lock nut engaging a proximal end of the inner member to limit movement of the inner member relative to and within the internal passage of the other swivelably fixed coupling. The lock nut could limit an extent of widening of the vertebral cut, and thereafter secure the upper portion relative to the lower portion and secure and maintain the width of the widened vertebral cut. Alternatively, a lock nut or stop could be integrally formed on a proximal end of the inner member. The lock nut or stop could limit movement of the inner member relative to and within the internal passage of the other swivelably fixed coupling, and due to the integral formation, provide a pre-determined extent of widening of the vertebral cut. The lock nut or stop would also thereafter secure the upper portion relative to the lower portion and secure and maintain the width of the widened vertebral cut.

In a still further aspect, the swivelable couplings could each be swivelably fixed within a respective one of the upper and the lower portions, each coupling having an internal passage therethrough. Movement of the inner member relative to and within the internal passage of the swivelable couplings would translate the upper portion away from the lower portion.

In this aspect, the internal passages of the swivelably fixed couplings could be threaded to engage exterior threads of the inner member and facilitate movement of the inner member relative thereto to translate the upper portion away from the lower portion. Further, the exterior threads of the inner member could be dual pitched, where the exterior threads of the inner member engaging the internal passage of one swivelably fixed coupling are reversed relative to the exterior threads of the inner member engaging the internal passage of the other swivelably fixed coupling. In addition, the inner bore of each of the upper and the lower portions could be conically shaped to accommodate angulation of the inner member during translation.

In still another aspect, the implant could include an upper portion and a lower portion, each having an inner bore, where the upper portion includes a widened inner bore over a proximal portion thereof and a narrower inner bore over a distal portion thereof. A rod-like inner member having bulbous ends would also be included, with the bulbous ends swivelable within a respective inner bore of the upper and the lower portion. In this aspect, one bulbous end could be swivelably fixed within the lower portion and the other bulbous end could be translatably and swivelably retained within the upper portion. Movement of the bulbous end in the upper portion could translate the upper portion away from the lower portion, about a vertebral cut, to widen the vertebral cut and expand the spinal canal. The swivelable action of the bulbous ends of the inner member during translation could allow angulation of the inner member, relative to a longitudinal axis of the implant, to accommodate the naturally occurring lateral offset of a vertebra during widening of the vertebral cut.

In this aspect, movement of the bulbous end of the inner member in the upper portion could be translation in a direction generally along a longitudinal axis of the implant. In addition, movement of the bulbous end of the inner member in the upper portion could occur within the widened inner bore of the upper portion in a direction from a proximal end of the widened inner bore to and finally abutting against a distal end of the widened inner bore.

This aspect might also include a retaining lock nut, threadably engaging inner walls of the widened inner bore of the upper portion, to advance and move the bulbous end of the inner member in the upper portion within the widened inner bore and to finally secure the bulbous end of the inner member in the upper portion against the distal end of the widened inner bore to secure the upper portion relative to the lower portion, after translation, to secure and maintain a width of the widened vertebral cut.

In a further aspect, an implant could include an upper portion, and lower portion and an inner member. The upper portion might include in an inner bore an upper coupling fixed therein but configured for swiveling. The upper coupling could have an internally threaded passage therethrough. The lower portion might include in an inner bore a lower coupling fixed therein but configured for swiveling. The inner member could be fixedly attached at one end to the lower coupling, with threads at the other end for engagement with the internally threaded passage of the upper coupling. Threadable movement of the inner member relative to the upper coupling causes the inner member to translate the upper portion away from the lower portion, about a vertebral cut, to widen the vertebral cut.

In a still further aspect, an implant could include an upper and a lower portion, each having an internal passage. In this aspect, at least one of the upper portion internal passage or the lower portion internal passage is offset from a central longitudinal axis of the upper and the lower portion. The implant further includes an inner member in communication with the upper and the lower portion. Movement of the inner member in relation to the upper and the lower portion causes the inner member to translate the upper portion away from the lower portion, about a vertebral cut, to widen the vertebral cut and to allow a lateral shift of the upper portion from the lower portion during vertebral cut widening. In this aspect, the inner member can be adapted to threadably engage at least a portion of the internal passage of either or each of the upper and the lower portions. Further, the upper portion could be mechanically secured to the lower portion by the inner member after widening of the vertebral cut to maintain the widened vertebral cut.

BRIEF DESCRIPTION OF THE DRAWINGS

For the purpose of illustrating the invention, there is shown in the drawings a form of the invention which is presently preferred; it being understood, however, that the invention is not limited to the precise arrangements and instrumentalities shown.

DETAILED DESCRIPTION OF THE ILLUSTRATED EMBODIMENTS

Figures 1, 2:
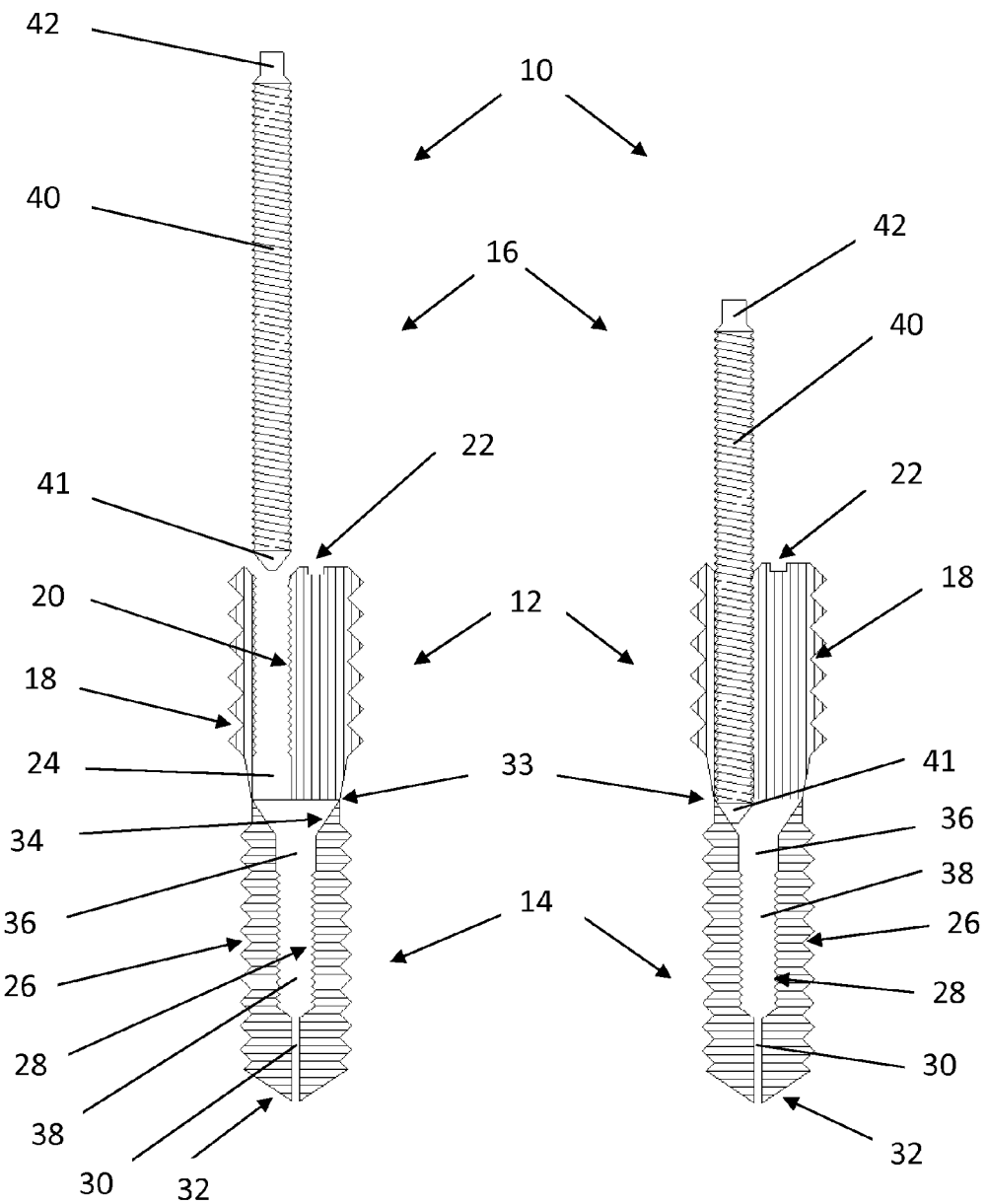
FIG. 1 illustrates an exploded, cross-section of one embodiment of a pedicle lengthening device of the present invention.
FIG. 2 illustrates a cross-sectional view of the device of FIG. 1, with a threaded rod entering an offset passage of a dorsal (upper) implant portion.

The present invention provides several novel devices that allow improved accommodation of the variations in pedicle anatomy and that allow for offset at the site of the pedicle osteotomy. These devices are believed to be particularly important in a situation where the pedicle has a high convergence angle. Various aspects of the embodiments disclosed herein involve a series of implantable devices having an upper and a lower portion bridged by a longitudinal (inner) member.

In one embodiment, the medical device comprises an upper and lower portion with internal threaded passages offset with respect to the central axis of the device. In use of this embodiment, a threaded member is threaded through the offset passages of the upper and lower portions of the device resulting in an elongation of the distance between the upper and lower portions of the device and a lateral shift (offset) between the devices.

In another embodiment, the upper and lower portions of the medical device have a threaded passages capable of angulating during the insertion of an internal dual-pitch threaded member. During usage of this device, the internal threaded passage this device is capable of allowing a lateral shift (offset) of the upper and lower portions of the device to accommodate the change in shape of the vertebrae during the pedicle lengthening process. In both cases the medical devices are intended to maintain the pedicles in an elongated state and allow bone healing across the site of the osteotomy.

In one aspect of the present invention, a novel pedicle lengthening device is disclosed which comprises an upper and lower portion that are introduced into an internal pedicle passage within the pedicle on opposite sides of a pedicle osteotomy (bone cut). The upper and lower portions of the medical device each have internal threaded passages which are offset with respect to the central longitudinal axis of the medical device. Varying embodiments are possible. The internal threaded passage of the upper portion could be offset relative to the central longitudinal axis, with the internal passage of the lower portion aligned with the central longitudinal axis. Or, the internal threaded passage of the lower portion could also be offset relative to the central longitudinal axis, perhaps on the opposite side of the central longitudinal axis relative to the upper portion. Other permutations of offset positioning are possible, as well dimensions of offset positioning, in each of the upper and lower portions, relative to the central longitudinal axis.

The pedicle lengthening device also comprises a threaded member which is inserted into the offset internal threaded passages of the upper and lower portions of the medical device. During insertion of the threaded member, the upper and lower portions of the device are distracted apart until the offset internal threaded passages of the upper and lower portions of the medical device align, allowing the threaded member to bridge the gap between the upper and lower portions of the medical device. The distraction of the space between the upper and lower portions of the device produces pedicle lengthening by expansion of the gap at the site of the pedicle osteotomy, with expansion of the spinal canal. In addition, the threaded member stabilizes the gap at the side of the pedicle osteotomy until healing of the pedicle gap occurs.

In another aspect of the present invention, a novel pedicle lengthening device is disclosed which comprises an upper and lower portion which is introduced into an internal pedicle passage and positioned on opposite sides of a pedicle osteotomy (bone cut). The medical device possesses an internal threaded passage capable of shifting its angulation with respect to the longitudinal axis of the upper and lower portions of the medical device. With threadable insertion of an internal threaded member, the upper and lower portions of the medical device are distracted apart, while allowing a lateral shift in the upper portion with respect to the lower portion of the medical device. Thus, the device shall allow offset of the upper and lower portions, in order to accommodate the altered anatomy of the lengthened pedicle. The threaded internal member shall stabilize the medical device in the distracted position, resulting in expansion of the pedicle gap and lengthening at the site of the pedicle osteotomy (bone cut). The medical device will be maintained to stabilize the expanded position of the pedicle osteotomy and to allow healing of the pedicle osteotomy.

In one instance, the device provides offset by internally threaded swiveling nuts in each of the upper and lower portions of the device. The swiveling nuts are each fixed within a respective upper or lower portion, but are movable (can swivel) within the respective upper or lower portion. In another instance, the swiveling nut is the only component of the upper or lower portion of the device to include internal threads, whereby the internal threaded member (having external threads) only engages the respective swiveling nut in each of the upper and lower portion of the device. That, together with the conical shape of the inner bore of each of the upper and lower portion of the device, provides the angular shift capability of the upper and lower portions, relative to the original, central longitudinal axis of the device, during distraction of the upper and lower portions from one another (and resulting pedicle lengthening).

In another instance, the device provides an internal threaded member, or jack screw, having a lower swivel ball, fixed but movable (swivelable) within the lower portion. This feature, together with an internally threaded swiveling nut in the upper portion, plus an enlarged inner bore in each of the upper and lower portion of the device, provides the angular shift capability of the upper and lower portions, relative to the original, central longitudinal axis of the device, during distraction of the upper and lower portions from one another (and resulting pedicle lengthening).

In another aspect of the present invention, use of any of the above exemplary implants provides a neutralization of the medially directed force vectors and an enhancement of the anteriorly directed force vector during the pedicle lengthening process.

The present invention has the following advantages over known devices for percutaneous pedicle lengthening:

(1) The device is easy to install percutaneously into the spinal pedicles;
(2) The devices is capable of neutralizing the medially directed force vector and promoting an anteriorly directed force vector during the pedicle lengthening process.
(3) The device enhances the pedicle lengthening process in pedicles with a high convergence angle;
(4) The device accommodates the changes in the pedicle anatomy during the pedicle lengthening process;
(5) The device produces a more biomechanically stable pedicle lengthening construct by reducing the stresses perpendicular to the longitudinal axis of the pedicle during pedicle lengthening; and
(6) The devices are simpler to manufacture compared to current designs for pedicle lengthening.

As noted above, one or more of the present inventors has recently disclosed and taught correction of spinal stenosis by expansion of the spinal canal (e.g., via lengthening of the spinal pedicles), as exemplified in U.S. Pat. Nos. 8,157,847; 7,166,107; and 6,358,254; and in U.S. Patent Application Publication Nos. 2011/0230915 and 2010/0168751. Each involves novel surgical procedures and implants for expansion of the spinal canal, for cutting and lengthening the spinal pedicles, and for fixating the vertebrae after expansion of the spinal canal, all for alleviating symptoms of spinal stenosis. Accordingly, each of U.S. Pat. Nos. 8,157,847; 7,166,107; and 6,358,254; and U.S. Patent Application Publication Nos. 2011/0230915 and 2010/0168751 are incorporated herein by reference. Each provides useful background information directed to procedures and implants for expansion of the spinal canal, generally, and for percutaneous techniques for use and insertion of pedicle lengthening screw implants, such as those detailed herein, and for related tools and cutting instruments for carrying out the percutaneous techniques and methodologies.

In view thereof, provided is a brief summary of techniques and procedures for expansion of the spinal canal. In one aspect, a method for correcting spinal stenosis is introduced where a spinal canal is enlarged by cutting a vertebra through one or both pedicles, separating the vertebral cut and then stabilizing the cut, allowing the vertebra to heal with the spinal canal expanded, permanently creating more space for the spinal nerves, thus relieving compression on the nerves.

In another aspect, the method of expanding the spinal canal includes drilling a passage or hollow tunnel into one or both pedicles of a vertebra, making a pedicle cut (osteotomy) from within the passage through to the spinal canal and to the outside of the vertebra, distracting (elongating) the osteotomy to expand the spinal canal, and then stabilizing the osteotomy.

In another aspect, the method of expanding the spinal canal includes the following steps: first, a guide wire is inserted into a central portion of the vertebral pedicles on each side of a vertebra. This and other method steps can be accomplished with the assistance of x-rays, fluoroscopy, CAT scan or computer assisted image guidance technology, which are well known in the art of spinal surgery.

Second, the guide wire is used to direct the position of a cannulated drill (drill with a central barrel or passage to allow introduction over the guide wire) into each of pedicles to form a passage or hollow tunnel in the central portion of each pedicle. At the conclusion of this step the pedicles comprise a hollow column of bone having a central passage and thin, cylindrical, bony walls.

Next, the vertebral pedicles are cut circumferentially, forming an upper portion and a lower portion. A side-cutting instrument can be introduced into the central passage in each pedicle to perform the circumferential cut. The side-cutting instrument has a cutting surface that projects radially outward so that the bony walls of each pedicle can be circumferentially cut. With both pedicles circumferentially cut, the vertebra is divided into an upper portion (including the spinous process, lamina, transverse process and articular processes) and a lower portion (including the vertebral body). The side-cutting instrument could include a rotating cutting burr or osteotome (chisel) as the cutting surface, both of which are well known in the art.

Finally, each osteotomy (site of the circumferential bone cut) is distracted (expanded). A specially designed implant, such as those of the present invention, can be used to distract the osteotomy. Generally, the implants of the present invention include an upper portion, a lower portion, and an inner member communicating and interacting with the upper and lower portion to distract the upper portion from the lower portion, thereby separating the vertebral cut and expanding the spinal canal. The implants of the present invention also provide for angulation of the inner member, relative to a longitudinal axis of the implant, to accommodate a change in shape of a vertebra that naturally occurs during widening of a vertebral cut.

Referring now to the drawings, where like numeral indicate like elements, there is shown in FIGS. 1-7 a first embodiment of a pedicle lengthening device 10 of the present invention. FIG. 1 illustrates an exploded, cross-sectional view of the pedicle lengthening device 10. Primarily including three components in this embodiment, the pedicle lengthening device 10 has an dorsal (upper) implant portion 12, a ventral (lower) implant portion 14, and an inner member (e.g., a threaded rod) 16.

The dorsal (upper) implant portion 12, in this embodiment, has external threads 18, an internally threaded inner bore (aka offset passage) 20, a driver connection 22, and a distal end 24 of the offset passage. The distal end 24 of the offset passage may be threadless over a portion thereof.

The ventral (lower) implant portion 14, in this embodiment, has external threads 26, an internally threaded inner bore 28, a cannulated passage 30, and a threaded end 32 (i.e., exterior threads extending to the end). Beginning at an upper surface 33 of the ventral implant 14, the inner bore 28 begins with a conical inner surface 34. Moving distally, the inner bore 28 includes a close tolerance passage 36, then a threaded passage portion 38. Of course, various alternatives are possible. The internally threaded inner bore 20 of the dorsal portion 12 could be offset relative to the central longitudinal axis of the device 10, with the internally threaded inner bore 28 of the lower portion 14 aligned with the central longitudinal axis of the device 10, as generally shown in FIGS. 1 and 2. Or, the internally threaded inner bore 28 of the lower portion 14 could also be offset relative to the central longitudinal axis of the device 10, perhaps on the opposite side of the central longitudinal axis relative to the inner bore 20 of the dorsal portion 12. Other permutations of offset positioning are possible, as well dimensions of offset positioning, in each of the dorsal and ventral portions 12, 14, relative to the central longitudinal axis of the device 10.

The inner member 16, in this embodiment a threaded rod, includes an outer threaded surface 40, a tapered end 41, and a proximal driver connection 42. FIG. 2 illustrates in cross-section the inner member 16 threaded through the inner bore 20 of the dorsal implant portion 12 with tapered end 41 of the inner member 16 entering and abutting the conical inner surface 34 portion of the inner bore 28 of the ventral implant portion 14.

Figures 3, 4, 5:
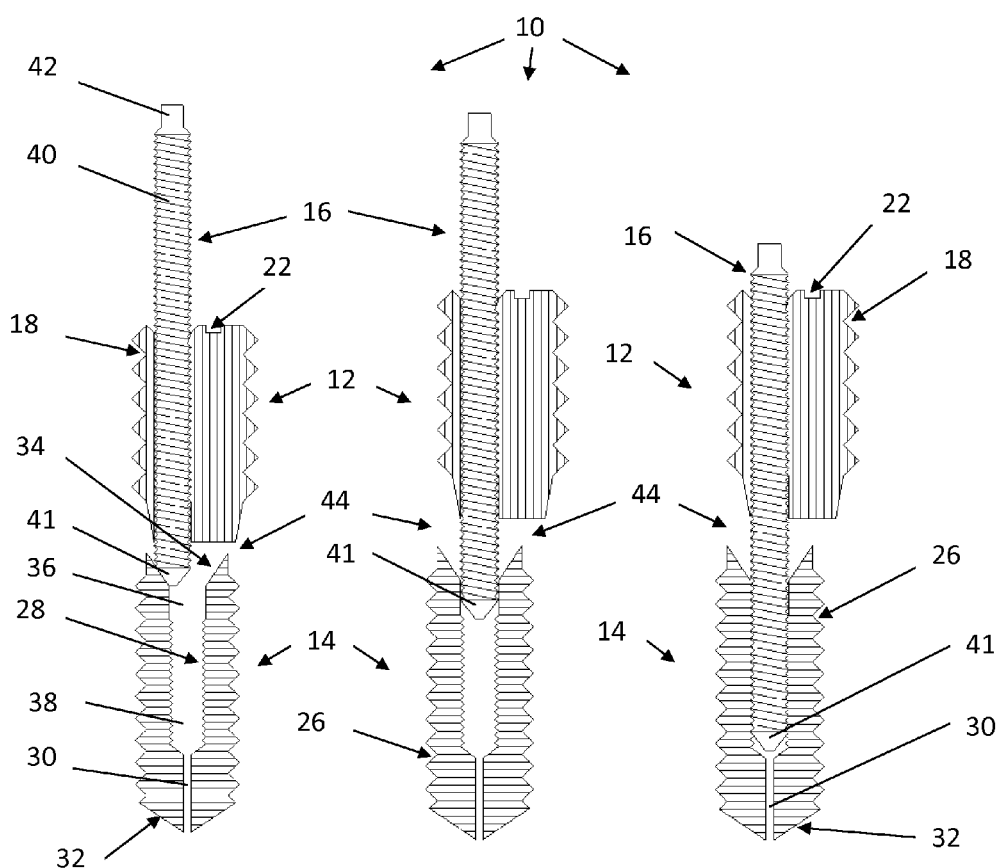
FIG. 3 illustrates a cross-sectional view of the device of FIG. 1, with the threaded rod contacting the ventral (lower) implant portion and producing a distracting force between the dorsal and ventral implant portions.
FIG. 4 illustrates a cross-sectional view of the device of FIG. 1, with the threaded rod causing an alignment of the dorsal (upper) and ventral (lower) implant offset passages, so as to allow the threaded rod to enter the internal offset passage of the ventral implant portion.
FIG. 5 illustrates a cross-sectional view of the device of FIG. 1, with the threaded rod securing the dorsal and ventral implant portions in a distracted position (space between the dorsal and ventral implant portions)

FIGS. 3-5 illustrate progression of the inner member 16 through the dorsal (upper) implant portion 12 and into the ventral implant (lower) portion 14 to distract the dorsal portion 12 away from the ventral portion 14 and to align the laterally offset inner bores 20, 28 of the dorsal and ventral portions 12, 14. The inner member 16 thereby bridges the gap between the dorsal and ventral portions 12, 14, where distraction space 44 produces pedicle lengthening by expansion of the pedicle osteotomy, thereby resulting in expansion of the spinal canal. Further, the inner member 16 stabilizes the gap at the side of the pedicle osteotomy until healing of the pedicle gap occurs.

Accordingly, FIG. 3 shows the tapered end 41 of the inner member 16 entering and abutting the conical inner surface 34 portion of the inner bore 28 of the ventral implant portion 14, thereby producing a distracting and laterally offsetting force between the dorsal and ventral portions 12, 14. FIG. 4 shows the inner member 16 causing an alignment of offset passages of the dorsal and ventral portions 12, 14, so as to allow the inner member 16 to then proceed into the ventral portion 14. Finally, FIG. 5 shows the inner member 16 abutting a distal end of the inner bore 28 of the ventral portion 14, to thereby complete the distracting force necessary to accomplish the desired separation (distraction space) 44 required to achieve pedicle lengthening. The inner member 16 secures the dorsal and the ventral portions 12, 14 in the desired distracted position (i.e., the separation space 44 between the dorsal and ventral portions 12, 14).

Figure 6:
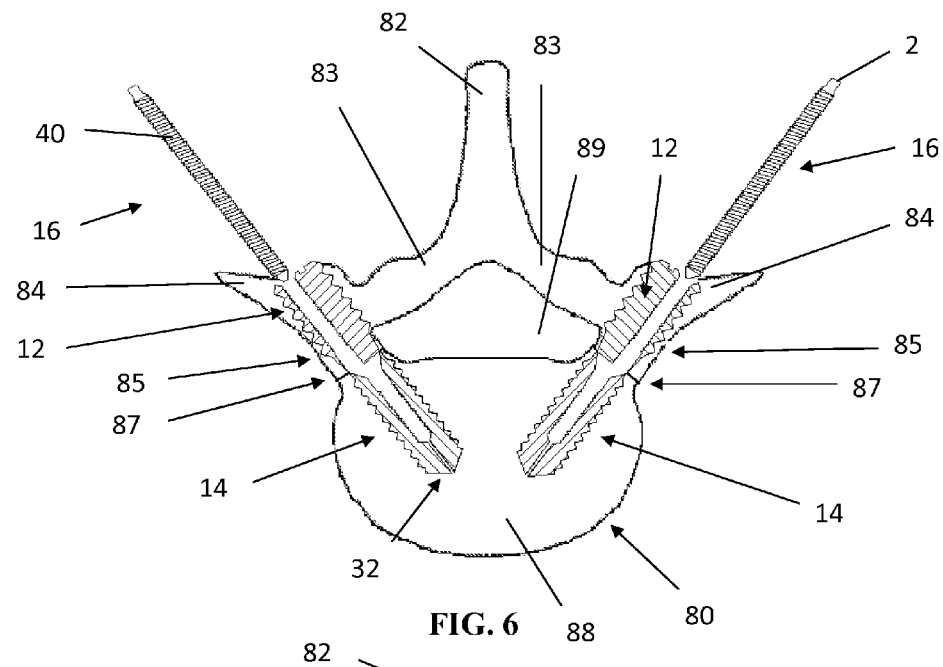
FIG. 6 illustrates a cross-sectional view of the device of FIG. 1, having the dorsal and the ventral implant portions inserted into vertebral pedicles and positioned on either side of pedicle osteotomies (bone cuts)
Figure 7:
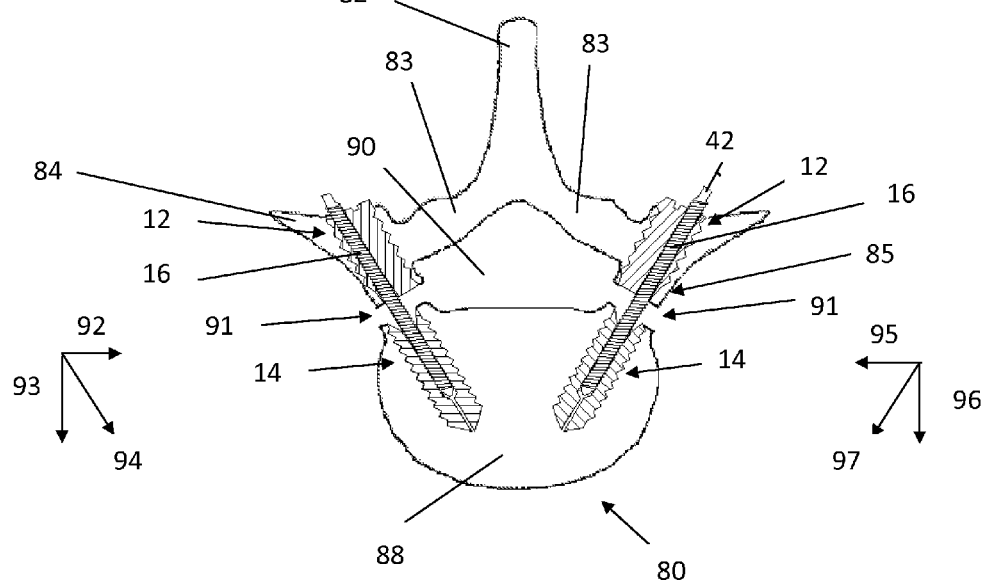
FIG. 7 illustrates a cross-sectional view of the vertebra of FIG. 6, where the dorsal and ventral implant portions of FIG. 1 are distracted apart and stabilized in the distracted position by action of the threaded rod resulting in expansion of the spinal canal.

FIGS. 6 and 7 illustrate the first embodiment of the pedicle lengthening device 10 of the present invention within a vertebra 80, showing the functionality and progression of the inner member 16 through the dorsal and ventral portions 12, 14 to lengthen a pedicle 85 of the vertebra 80, as detailed above for FIGS. 3-5. The vertebra 80 includes a spinous process 82, a lamina 83, a transverse process 84, the pedicle 85 and spinal canal 89.

For example, FIG. 6 illustrates the dorsal and the ventral portions 12, 14 of the pedicle lengthening device 10 inserted into a passage drilled into vertebral pedicles 85, with the dorsal and the ventral portions 12, 14 positioned on either side of a respective pedicle osteotomy (bone cut) 87. FIG. 7 illustrates the dorsal and the ventral portions 12, 14 distracted apart by inner member 16 to separate the pedicle osteotomy 87 (creating a pedicle gap 91), thereby lengthening the pedicle 85, whereby the dorsal and the ventral portions 12, 14 are laterally offset and stabilized in the distracted position by action of the inner member 16 within the dorsal and the ventral portions 12, 14, resulting in an expanded spinal canal 90. FIG. 7 also illustrates two vector diagrams for appreciation of the offset and distraction forces occurring during functionality of the pedicle lengthening device 10. One vector diagram illustrates a right medial vector 92, a right anterior vector 93 and the right distraction vector 94. The second vector diagram illustrates a left medial vector 95, a left anterior vector 96 and the left distraction vector 97.

Figure 8:
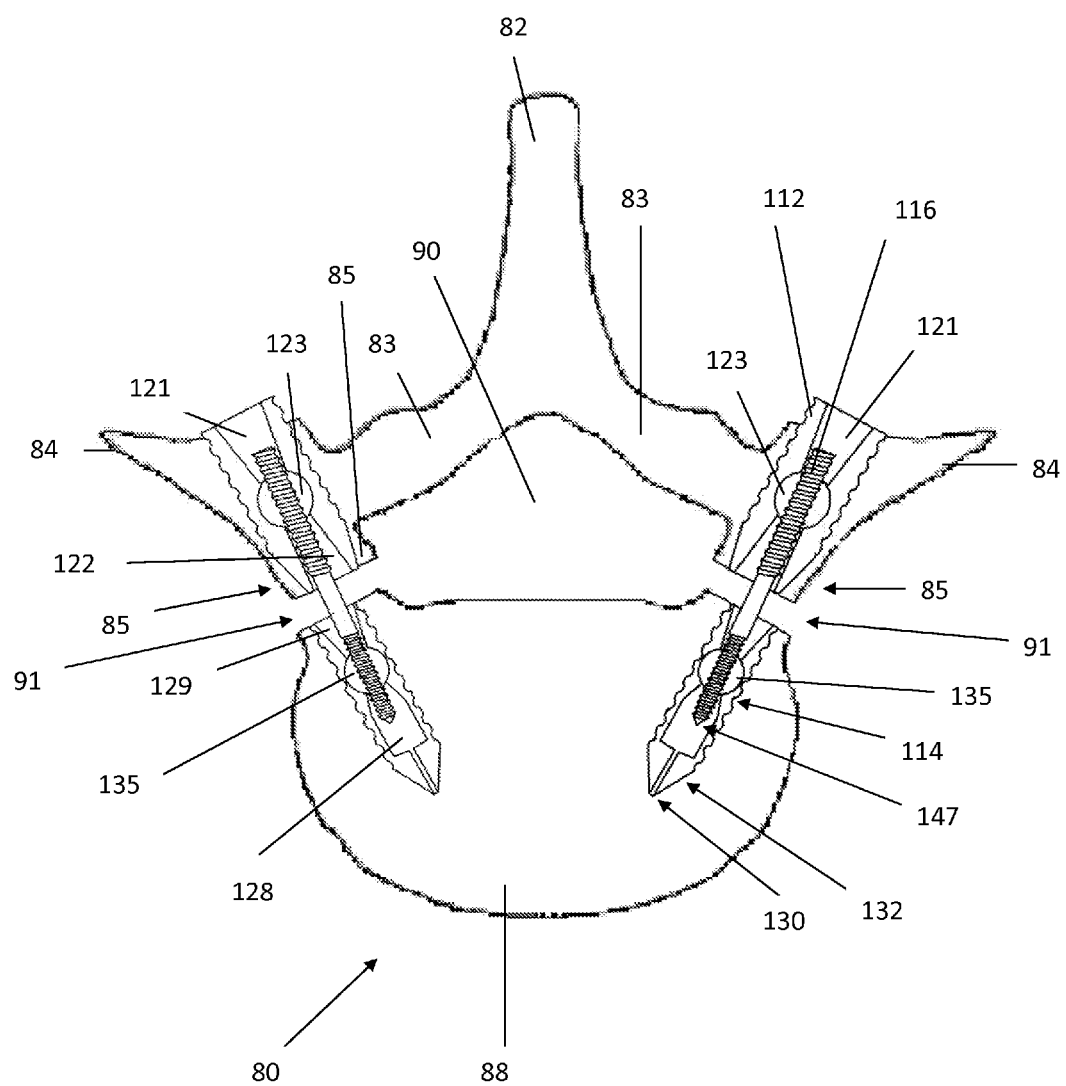
FIG. 8 illustrates a cross-sectional view of a vertebra, where dorsal and ventral implant portions of another embodiment of the present invention are distracted apart and stabilized in the distracted position by action of an inner member (jack screw) angulating relative to the longitudinal axis of the dorsal and ventral implant portions of the device, resulting in expansion of the spinal canal that accommodates natural pedicle lengthening offset.

FIGS. 8-12 illustrate a second embodiment of a pedicle lengthening device 110 of the present invention. FIG. 8 shows the second embodiment of the pedicle lengthening device 110 of the present invention within a vertebra 80, showing the functionality and progression of the inner member 116 through the dorsal and ventral portions 112, 114 to lengthen a pedicle 85 of the vertebra 80. FIG. 8 also illustrates capability of the inner member 116 to angulate during distraction to provide for lateral offset of the dorsal portion 112 relative to the ventral portion 114 during pedicle lengthening. In this embodiment, the inner member 116 (aka jack screw) angulates relative to a longitudinal axis of the dorsal and the ventral implant portions 112, 114 (in their pre-elongated state) to accommodate the natural pedicle lengthening offset occurring during expansion of the spinal canal.

Figures 9, 10:
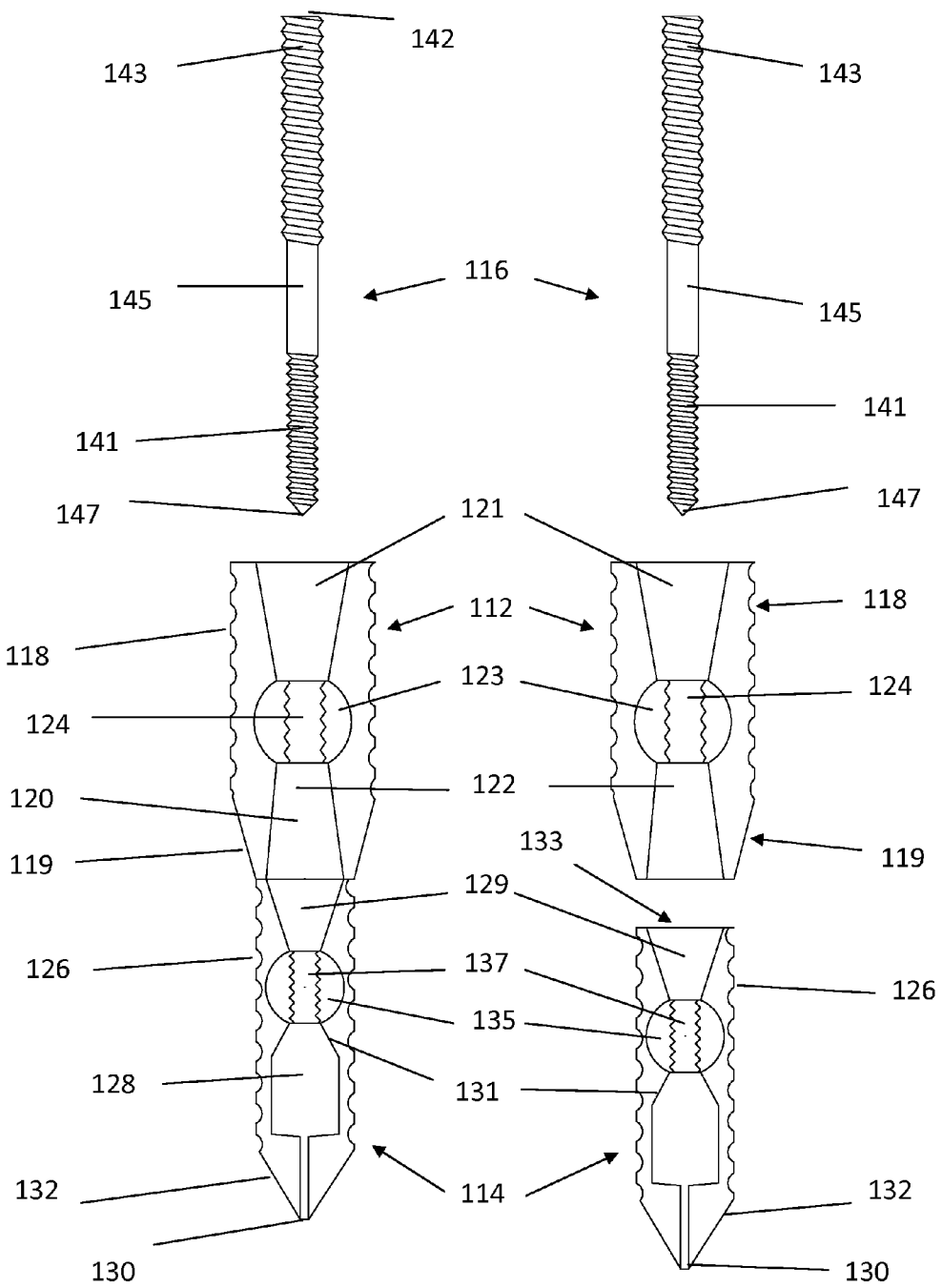
FIG. 9 illustrates a cross-sectional view of the FIG. 8 embodiment of the present invention, with the inner member withdrawn from the device, showing the dorsal and ventral implant portions of the device in a pre-elongated (pre-distracted) position.
FIG. 10 illustrates a cross-sectional view of the FIG. 8 embodiment of the present invention, with the inner member withdrawn from the device, showing the dorsal and ventral implant portions of the device a elongated (distracted) position.

FIG. 9 illustrates a cross-sectional view of second embodiment of a pedicle lengthening device 110, with the inner member 116 withdrawn from the device 110, showing the dorsal and the ventral portions 112, 114 in their pre-elongated (pre-distracted) position. FIG. 10 is similar, but shows the dorsal and the ventral portions 112, 114 in an elongated (distracted) position.

The inner member 116, or jack screw, in this embodiment, includes an outer threaded lower surface 141, a proximal driver connection 142, an outer threaded upper surface 143, an unthreaded middle outer surface 145, and a tapered and threaded end 147. The inner member 116 may be dual pitched, where the threads of the outer threaded lower surface 141 are reversed relative to the threads of the outer threaded upper surface 143.

The dorsal (upper) implant portion 112, in this embodiment, has external threads 118 on a cylindrical portion thereof, and an unthreaded conical exterior surface 119 at a distal end thereof. Also included is an inner bore 120, having an upper, conically shaped tolerance hole 121 and a lower, conically shaped tolerance hole 122. The inner bore 120 also includes therein a swivelably fixed coupling 123 having an internally threaded central passage 124. In this embodiment, the inner bore 120 is not threaded, but for the internally threaded central passage 124 of the swivelably fixed coupling 123 (which can be spherically shaped and press fit therein).

The ventral (lower) implant portion 114, in this embodiment, has an upper surface 133, external threads 126 on a cylindrical portion thereof, a cannulated passage 130, and a threaded end 132 (i.e., exterior threads extending to the end). Also included is an inner bore 128, having an upper, conically shaped tolerance hole 129 and a lower, conically shaped tolerance hole 131. The inner bore 128 also includes therein a swivelably fixed coupling 135 having an internally threaded central passage 137. In this embodiment, the inner bore 128 is also not threaded, but for the internally threaded central passage 137 of the swivelably fixed coupling 135 (which can be spherically shaped). In this embodiment, the dorsal (upper) implant portion 112 may have an exterior diameter generally larger than that of the ventral (lower) implant portion 114.

Figures 11, 12:
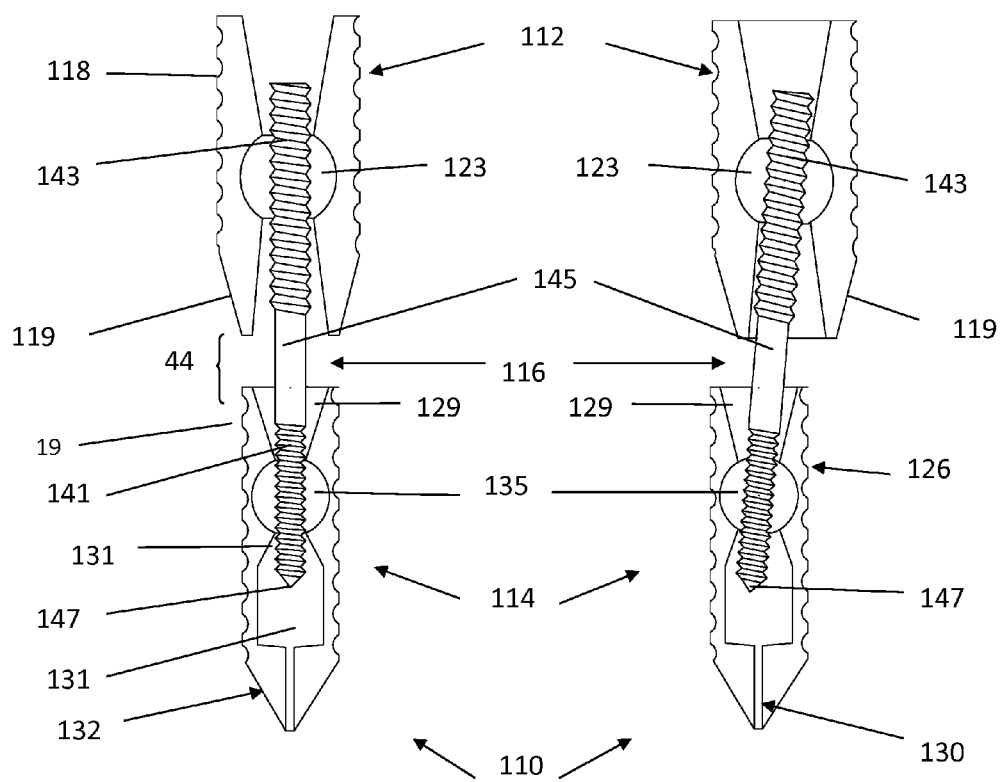
FIG. 11 illustrates a cross-sectional view of the FIG. 8 embodiment of the present invention, with the inner member inserted into the device, showing the dorsal and ventral implant portions distracted apart and stabilized in the distracted position by the inner member.
FIG. 12 illustrates a cross-sectional view of the FIG. 8 embodiment of the present invention, with the inner member inserted into the device, showing the dorsal and ventral implant portions distracted apart and stabilized in the distracted position by the action of the inner member angulating relative to the axes of the dorsal and ventral implant portions of the device.

FIGS. 11 and 12 illustrate progression of the inner member 116 through the dorsal (upper) implant portion 112 and into the ventral implant (lower) portion 114 to distract the dorsal portion 112 away from the ventral portion 114, where the inner member 116 also angulates (relative to the longitudinal axis of the device 110 in its pre-elongated state) during distraction to provide for lateral offset of the dorsal portion 112 relative to the ventral portion 114 during pedicle lengthening. Inner member 116 angulation accommodates the natural offset that occurs at the pedicle osteotomy site during pedicle lengthening and expansion of the spinal canal. The inner member 116 also bridges and stabilizes the gap (the distraction space 44) between the dorsal and the ventral portions 112, 114. As such, FIG. 11 therefore illustrates in cross-section the inner member 116 inserted into the device 110, showing the dorsal and the ventral implant portions 112, 114 distracted apart and stabilized in the distracted position by the inner member 116, with FIG. 12 showing the same, but also illustrating the angulating action of the inner member 116, relative to the longitudinal axes of the dorsal and the ventral portions 112, 114 of the device 110, via the swivelably fixed couplings 123, 135.

Figure 13:
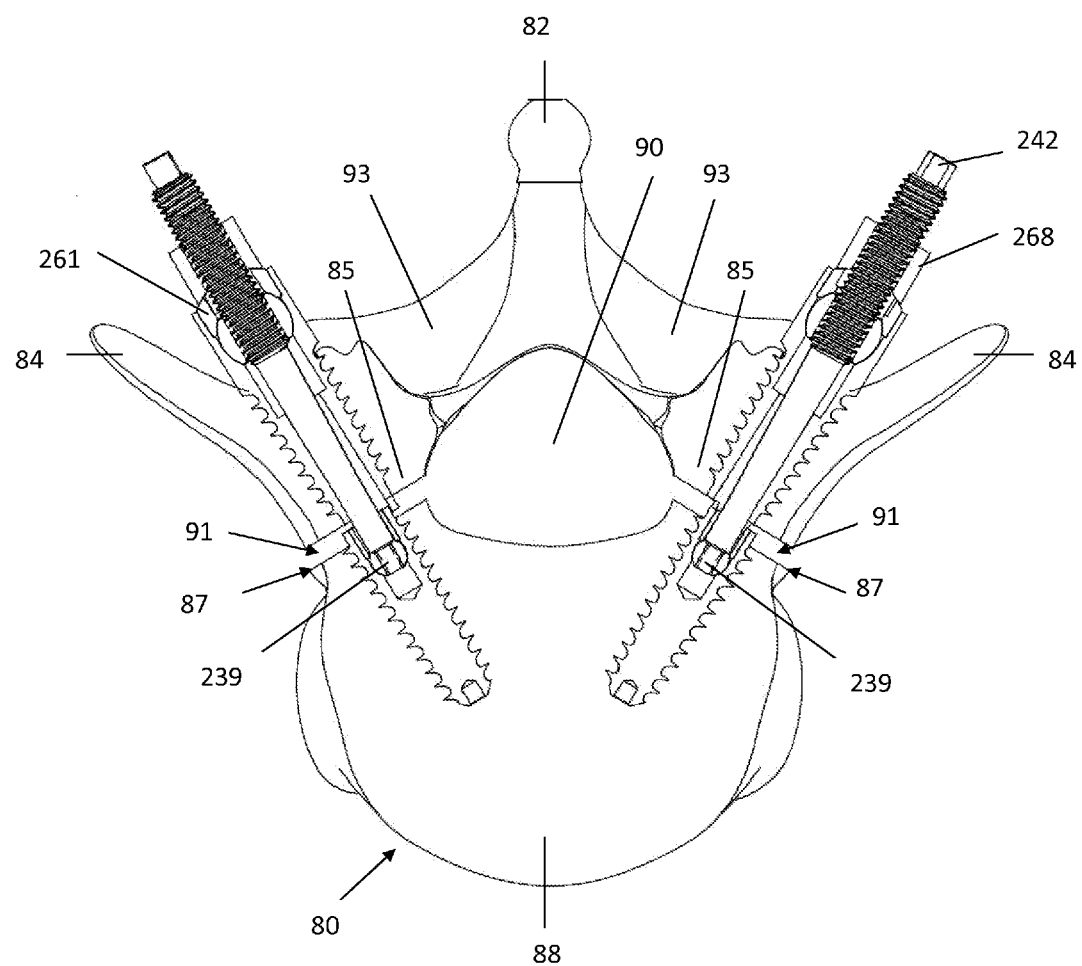
FIG. 13 illustrates a cross-sectional view of a vertebra, where dorsal and ventral implant portions of still another embodiment of the present invention are distracted apart and stabilized in the distracted position by action of an inner member pivoting and angulating internally within the device during distraction, resulting in the expansion of the spinal canal that accommodates natural pedicle lengthening offset.
Figures 14, 15:
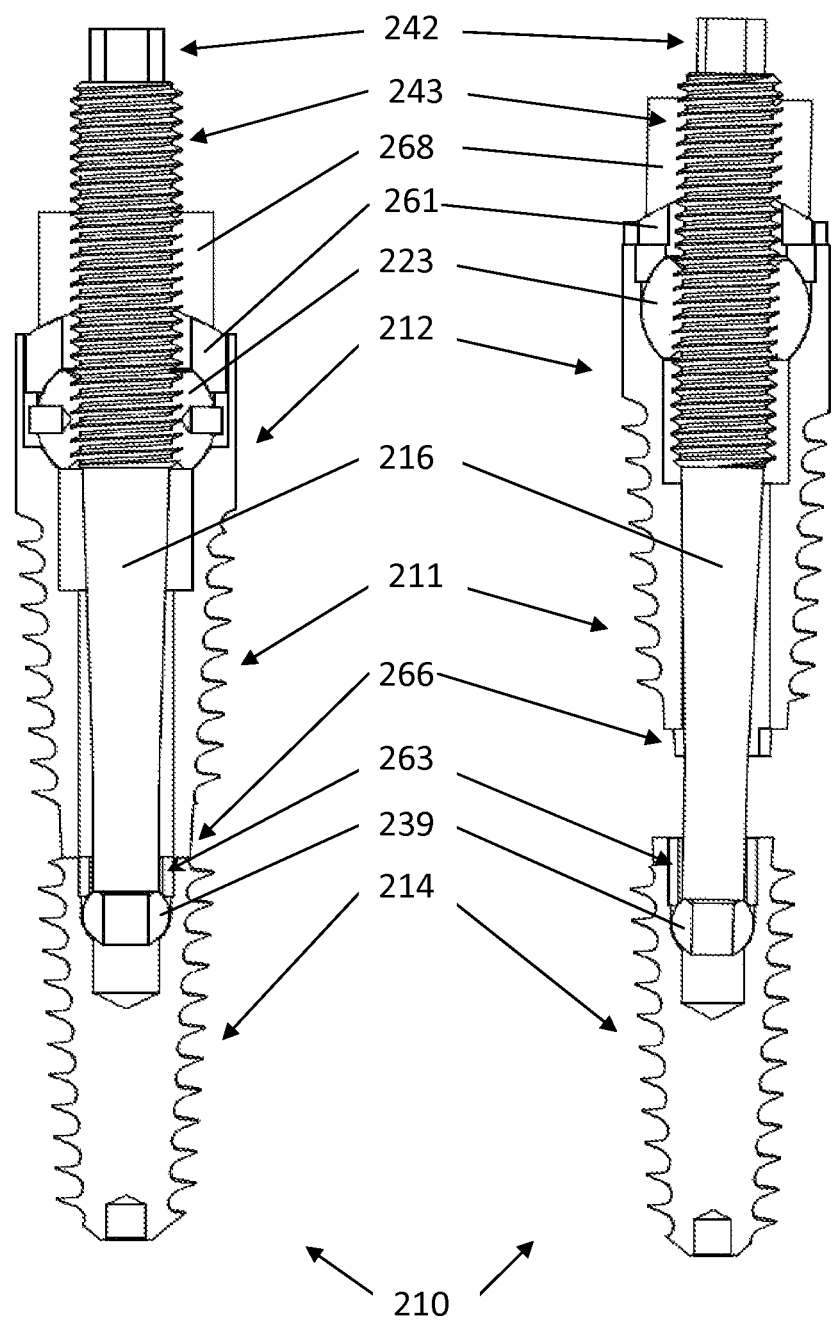
FIG. 14 illustrates a cross-sectional view of the FIG. 13 embodiment of the present invention, showing the inner member swivelably fixed inside of the ventral (lower) implant portion, securing the dorsal and ventral implant portions in the pre-elongated (non-expanded) position.
FIG. 15 illustrates a cross-sectional view of the FIG. 13 embodiment of the present invention, showing the inner member swivelably fixed inside of the ventral implant portion, securing the dorsal and ventral implant portions in the distracted (elongated) position, and showing a lateral positional shift of the dorsal and ventral implant portions (offset) with respect to an initial (see FIG. 14) longitudinal axis of the device.

FIGS. 13-15 illustrate a third embodiment of a pedicle lengthening device 210 of the present invention. FIG. 13 shows the third embodiment of the pedicle lengthening device 210 of the present invention within a vertebra 80, showing the functionality and progression of the inner member 216 through the dorsal and ventral portions 212, 214 to lengthen a pedicle 85 of the vertebra 80. FIG. 13 illustrates capability of the inner member 216 of this third embodiment to also angulate during distraction to provide for lateral offset of the dorsal portion 212 relative to the ventral portion 214 during pedicle lengthening. In this embodiment, the inner member 216 (aka swiveling screw) also angulates relative to a longitudinal axis of the dorsal and the ventral implant portions 212, 214 (relative to their pre-elongated state) to accommodate the natural pedicle lengthening offset occurring during expansion of the spinal canal. As such, FIG. 13 illustrates in cross-section the dorsal and the ventral implant portions 212, 214 distracted apart and stabilized in the distracted position (across a pedicle gap 91) by action of the inner member 216 pivoting and angulating internally within the device during distraction, resulting in the expansion of the spinal canal that accommodates natural pedicle lengthening offset.

FIG. 14 illustrates in cross-section the third embodiment of the pedicle lengthening device 210, showing the inner member 216 swivelably fixed inside of the ventral (lower) implant portion 214, threadably securing the dorsal implant portion 212 thereto in a pre-elongated (non-expanded) position. FIG. 15 illustrates the third embodiment device 210 in an elongated position (distracted or expanded state). Upon expansion, the inner member 216 is still swivelably fixed inside of the ventral portion 214, but the inner member 216 has threadably distracted the dorsal portion 212 away from the ventral portion 214, and threadably secures the dorsal and the ventral portions 212, 214 in the distracted (elongated) position. FIG. 15 also shows the lateral positional shift (offset) of the dorsal and the ventral implant portions 212, 214, with respect to an initial (see FIG. 14) longitudinal axis of the pre-elongated dorsal and ventral portions 212, 214, via angulation of the inner member 216.

In FIGS. 14 and 15, the inner member 216, or swiveling screw in this embodiment, includes an a proximal driver connection 242, an outer threaded upper surface 243, and a distal end permanently connected to a fixed, swivelable coupling 239 within the ventral portion 214. The permanent connection of the distal end of the inner member 216 to the swivelably fixed coupling 239 could be by weld, press fit, or the like.

The dorsal (upper) implant portion 212, in this embodiment, has external threads over a cylindrical portion, where the exterior cylindrical surface may be conically shaped 211 at a distal end thereof. Also included is an inner bore having therein a swivelably fixed coupling 223 with an internally threaded central passage. In this embodiment, the inner bore is not threaded, but for the internally threaded central passage of the swivelably fixed coupling 223 (which can be spherically shaped).

The dorsal portion 212 can also include an upper retaining ring 261, having external threads about its exterior circumference, that can be employed to secure the fixed swiveling coupling 223 within the inner bore of the dorsal portion 212. The external threads of the upper retaining ring 261 engage internal threads located within a proximal end of the inner bore of the dorsal implant portion 212. Further, the distal end of the dorsal portion 212 can include a locking mechanism 266 to engage a like mechanism 266 on the proximal end of the ventral portion 214 (when the device 210 is in the pre-elongated state). The locking mechanism 266 can be in the form of matching and engageable (e.g., male/female, etc.) teeth, shapes or cutouts. During the threadable insertion of the device 210 into a drilled pedicle passage, the locking mechanism 266 relieves the device 210 of torsional stress otherwise absorbed by the inner member 216 and the fixed swivelable coupling 239 of the ventral portion 214 (which otherwise solely stabilize the dorsal portion 212 to the ventral portion 214).

The ventral (lower) implant portion 214, in this embodiment, has external threads on a cylindrical portion thereof, the cylindrical portion also possibly being conically shaped. Also included is a small inner bore housing the fixed swivelable coupling 239 (which can be spherically shaped). In this embodiment, the device 210 can have a continuous exterior taper from proximal end of the dorsal portion 212 to the distal end of the ventral portion 214. A lower retaining ring 263, having external threads about its exterior circumference, can be employed to secure the fixed swiveling coupling 239 within the inner bore of the ventral portion 214. The external threads of the lower retaining ring 263 engage internal threads located within a proximal end of the inner bore of the ventral portion 214. The retaining ring 263 could also be press fit therein, or similar connection known in the art.

Lastly, a lock nut 268 can threadably engage the proximal end of the outer threaded upper surface 243 of the inner member 216. The lock nut 268 can be positioned on the inner member 216 to limit the distraction space (pedicle gap 91) and to help secure the dorsal portion 212 to the ventral portion 214 upon completion of pedicle lengthening. Alternatively, the lock nut 268 could be integrally formed on the proximal end of the inner member 216, thereby providing a pre-determined (upon device 210 manufacture) pedicle gap 91 for the device 210.

Figures 16, 17:
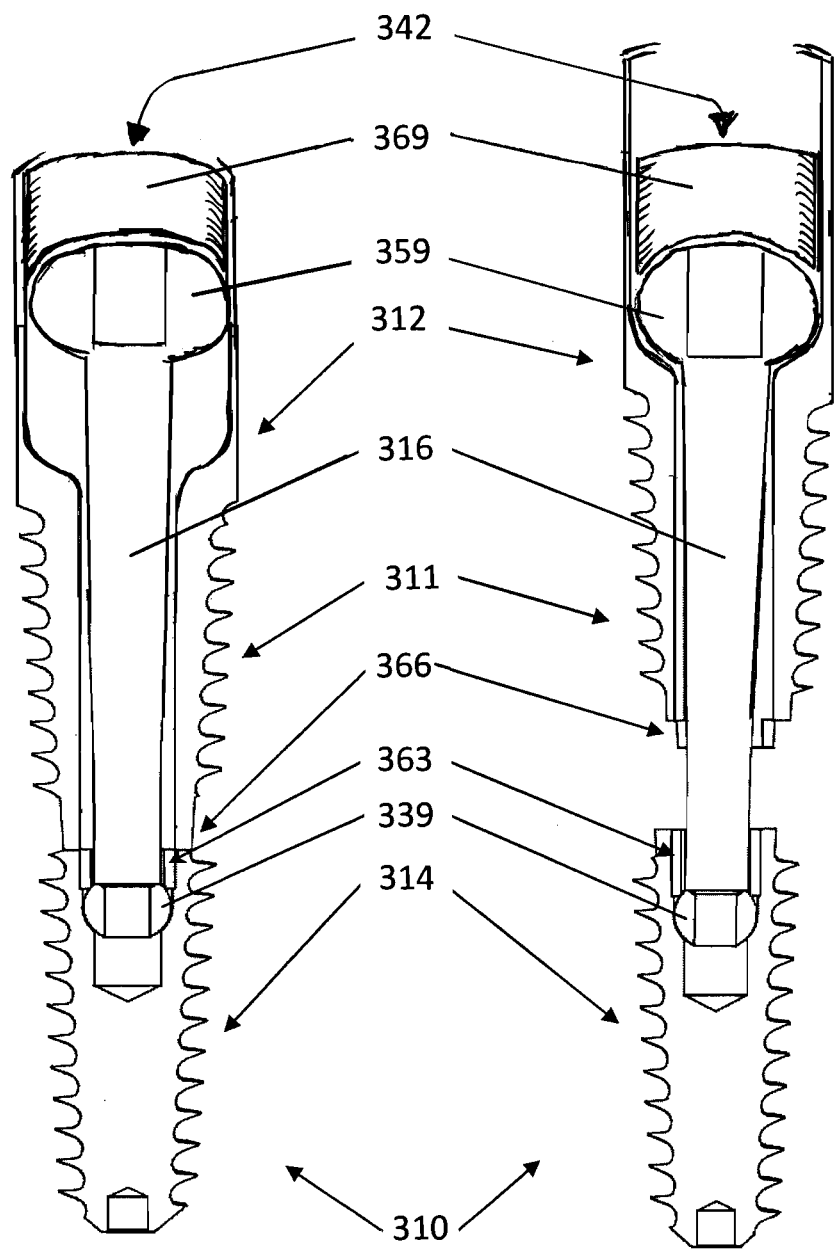
FIG. 16 illustrates a cross-sectional view of a still further embodiment of the present invention, showing the inner member swivelably fixed inside of the ventral (lower) implant portion and translatably and swivelably retained inside the dorsal (upper) implant portion, where the dorsal and ventral implant portions are shown in the pre-elongated (non-expanded) position.
FIG. 17 illustrates a cross-sectional view of the FIG. 16 embodiment of the present invention, showing the inner member swivelably fixed inside of the ventral implant portion, showing the inner member after translation within the dorsal (upper) implant portion, where the dorsal and ventral implant portions are now in the distracted (elongated) position, and showing a slight lateral positional shift of the dorsal and ventral implant portions (offset) with respect to an initial (see FIG. 16) longitudinal axis of the device.

FIGS. 16 and 17 illustrate a fourth embodiment of a pedicle lengthening device 310 of the present invention. The fourth embodiment of the pedicle lengthening device 310 also functions to lengthen a pedicle via action of an inner member 316 relative to dorsal and ventral portions 312, 314. The inner member 316 of this fourth embodiment also angulates during distraction to provide for lateral offset of the dorsal portion 312 relative to the ventral portion 314 during pedicle lengthening. In this embodiment, the inner member 316 (aka dog bone) translates within, and along a longitudinal axis of, the dorsal portion 312 to distract the dorsal portion 312 from the ventral portion 314 to create the pedicle gap 91, as will be detailed below.

FIG. 16 illustrates in cross-section the fourth embodiment of the pedicle lengthening device 310, showing the inner member 316 swivelably fixed inside of the ventral (lower) implant portion 314, and translatably and swivelably positioned at and within a proximal end of a widened bore hole in the dorsal (upper) implant portion 312. The device 310 is shown in a pre-elongated (non-expanded) position. FIG. 17 illustrates the fourth embodiment device 310 in an elongated position (distracted or expanded state). Upon expansion, the inner member 316 is still swivelably fixed inside of the ventral portion 314, but the inner member 316 has longitudinally translated to a distal end of the widened bore hole of the dorsal (upper) implant portion 312. Accordingly, the dorsal portion 312 is distracted away from the ventral portion 314. A retaining lock nut 369 threadably secures the translatable and swivelable upper coupling 359 (at a proximal end of the inner member 316) within and against the distal end of the widened bore hole of the dorsal portion 312. Therefore, the retaining lock nut 369 acts to secure and fix the dorsal and the ventral portions 312, 314 in the distracted (elongated) position. FIG. 17 also shows a slight lateral positional shift (offset) of the dorsal and the ventral implant portions 312, 314, with respect to an initial (see FIG. 16) longitudinal axis of the pre-elongated dorsal and ventral portions 312, 314, via angulation of the inner member 316.

In FIGS. 16 and 17, the inner member 316, or dog bone in this embodiment (because of its rod shape with two bulbous ends), includes at its distal end a swivelably fixed lower coupling 339 within the ventral portion 314, and at its proximal end a translatable and swivelable upper coupling 359 within the dorsal portion 312. The swivelably fixed lower coupling 339 can have a diameter smaller than that of the translatable and swivelable upper coupling 359.

The dorsal (upper) implant portion 312, in this embodiment, has external threads over a cylindrical portion, where the exterior cylindrical surface may be conically shaped 311 at a distal end thereof. Also included is a narrow inner bore at a distal end thereof and a widened inner bore at a proximal end thereof. The dorsal portion 312 houses the translatable and swivelable upper coupling 359 (of the inner member 316) within its widened inner bore. The widened inner bore includes internal threads to engage external threads of the retaining lock nut 369. The translatable and swivelable upper coupling 359 can be spherically shaped. The distal end of the dorsal portion 312 can similarly include a locking mechanism 366 to engage a like mechanism 366 on the proximal end of the ventral portion 314 (when the device 310 is in the pre-elongated state). The locking mechanism 366 can similarly be in the form of matching and engageable (e.g., male/female, etc.) teeth, shapes or cutouts, to relieve torsional stress during threadable insertion of the device 310 into a drilled pedicle passage.

The ventral (lower) implant portion 314, in this embodiment, has external threads on a cylindrical portion thereof, the cylindrical portion also possibly being conically shaped. Also included is a small inner bore housing the swivelably fixed lower coupling 339 (which can be spherically shaped). In this embodiment, the device 310 can similarly have a continuous exterior taper from proximal end of the dorsal portion 312 to the distal end of the ventral portion 314. A lower retaining ring 363, having external threads about its exterior circumference, can be employed to secure the swivelably fixed lower coupling 339 within the inner bore of the ventral portion 314. The lower retaining ring 363 could also be press fit therein.

Lastly, the retaining lock nut 369 includes a driver connection 342 (e.g., hex head driver slot) to provide threadable longitudinal translation of the retaining lock nut 369 to move the translatable and swivelable upper coupling 359 in a distal direction to distract the dorsal portion 316 from the ventral portion 314 to widen the pedicle gap 91. Upon full distraction, the retaining lock nut 369 secures the upper coupling 359 against the narrowing distal end of the widened bore hole of the dorsal (upper) portion 312 to fix the dorsal portion 312 relative to the ventral portion 314. In this embodiment, a length of the widened bore hole of the dorsal portion 312 (relative to the retaining lock nut 369 and upper coupling 359 therein) can be pre-determined (upon device 310 manufacture) to ensure an exact distraction space (pedicle gap 91) for the device 310.

These and other advantages of the present invention will be apparent to those skilled in the art from the foregoing specification. Accordingly, it will be recognized by those skilled in the art that changes or modifications may be made to the above described embodiments without departing from the broad inventive concepts of the invention. Any specific dimensions provided for any particular embodiment of the present invention are for illustration purposes only. It should therefore be understood that this invention is not limited to the particular embodiments described herein, but is intended to include all changes and modifications that are within the scope and spirit of the invention and claims, and of the problems solved by illustrated embodiments.

What is claimed is:

1. An implant for expanding a spinal canal, comprising:
   an upper portion and a lower portion, each having an inner bore;
   an inner member extending into the inner bore of, and interacting with, each of the upper and the lower portions;
   one swivelable coupling located within the inner bore of each of the upper and the lower portions, each swivelable coupling communicating with the inner member;
   wherein: the inner bore of the upper portion defines an implant longitudinal axis;
   at least one swivelable coupling is retained, fixed from translation along the implant longitudinal axis, relative to the inner bore;
   rotating the inner member about the implant longitudinal axis translates the upper portion away from the lower portion, along the implant longitudinal axis, about a vertebral cut, to widen the vertebral cut, thereby expanding the spinal canal; and
   each swivelable coupling, tiltable relative to the implant longitudinal axis, during an entirety of the translation of the upper portion away from the lower portion along the implant longitudinal axis, angulates the entire inner member relative to the implant longitudinal axis to accommodate a lateral offset of a vertebra occurring during the widening of the vertebral cut.

2. The implant of claim 1, wherein the inner bore of each of the upper and the lower portions is conically shaped, narrower adjacent to the swivelable coupling, to accommodate angulation of the inner member during translation of the upper portion away from the lower portion along the implant longitudinal axis, whereby the inner member angulation compensates for a lateral shift of the upper portion relative to the lower portion during the translation.

3. The implant of claim 1, wherein one swivelable coupling is free to translate along the implant longitudinal axis within the inner bore of a respective one of the upper and the lower portions.

4. The implant of claim 3, further comprising a retaining ring placed within the inner bore of the respective one of the upper and the lower portions to secure the swivelable coupling therein, and to continue to allow the tiltable action of the swivelable coupling relative to the implant longitudinal axis.

5. The implant of claim 3, wherein the one swivelable coupling free to translate along the implant longitudinal axis within the inner bore of the respective one of the upper and the lower portions, moves longitudinally within a widened portion of the inner bore, from one end of the widened portion to and finally abutting against another end of the widened portion, to translate the upper portion away from the lower portion, about the vertebral cut, to widen the vertebral cut, thereby expanding the spinal canal.

6. The implant of claim 1, wherein the swivelable couplings are each retained within the inner bore, fixed from translation, and each has an internal passage completely through the coupling, accepting the inner member completely therethrough, where movement of the inner member relative to and within the internal passages translates the upper portion away from the lower portion.

7. The implant of claim 6, wherein each internal passage is threaded and engages exterior threads of the inner member to facilitate rotation of the inner member therein to translate the upper portion away from the lower portion.

8. The implant of claim 1, wherein the swivelable couplings are each retained, fixed from translation, within a respective one of the upper and the lower portions, where one swivelable coupling is permanently attached to one end of the inner member and the other swivelable coupling has an internal passage completely through the swivelable coupling, accepting the inner member completely therethrough, where movement of the inner member relative to and within the internal passage of the other swivelable coupling translates the upper portion away from the lower portion.

9. The implant of claim 8, wherein the internal passage of the other swivelable coupling is threaded and engages exterior threads of the inner member to facilitate rotation of the inner member therein to translate the upper portion away from the lower portion.

10. The implant of claim 8, further comprising a lock nut, engageable with a proximal end of the inner member to limit movement of the inner member relative to and within the internal passage of the other swivelable coupling to limit translation of the upper portion away from the lower portion, thereby limiting an extent of widening of the vertebral cut, and thereafter securing the upper portion relative to the lower portion and securing and maintaining a width of the widened vertebral cut.

11. The implant of claim 8, wherein the upper and the lower portions are each cylindrically shaped, including external threads, the upper and lower portions, aligned end to end longitudinally, defining a continuous, conical exterior taper from a proximal portion of the upper portion to a distal end of the lower portion.

12. The implant of claim 1, wherein the swivelable couplings are each fixed from translation along the implant longitudinal axis, and each swivelable coupling has an internal passage therethrough, wherein rotation of the inner member relative to and within the internal passage of the swivelable couplings translates the upper portion away from the lower portion.

13. The implant of claim 12, wherein the internal passages of the swivelable couplings are threaded and engage exterior threads of the inner member to facilitate rotation of the inner member relative thereto to translate the upper portion away from the lower portion.

14. The implant of claim 13, wherein the exterior threads of the inner member are dual pitched, where the exterior threads of the inner member engaging the internal passage of one swivelable coupling are reversed relative to the exterior threads of the inner member engaging the internal passage of the other swivelable coupling.

15. The implant of claim 12, wherein the inner bore of each of the upper and the lower portions is conically shaped, narrower adjacent to the swivelable coupling, to accommodate angulation of the inner member during translation of the upper portion away from the lower portion along the implant longitudinal axis, whereby the inner member angulation compensates for a lateral shift of the upper portion relative to the lower portion during the translation.

16. An implant for expanding a spinal canal, comprising:
an upper portion and a lower portion, each having an inner bore, wherein the upper portion is proximal to the lower portion, and wherein the upper portion includes a widened inner bore over a proximal portion thereof and a narrower inner bore over a distal portion thereof;
an inner member extending into the inner bore of, and interacting with, each of the upper and the lower portions;
one bulbous, swivelable coupling located in the inner bore of each of the upper and the lower portions, each bulbous, swivelable coupling communicating with a respective end of the inner member;
wherein: the inner bore of the upper portion defines an implant longitudinal axis;
each bulbous, swivelable coupling is rotatable and tiltable relative to the implant longitudinal axis;
the bulbous, swivelable coupling of the upper portion is free to translate along the implant longitudinal axis within the widened, proximal portion of the inner bore of the upper portion;
movement of the bulbous, swivelable coupling of the upper portion, within and relative to the widened, proximal portion of the inner bore of the upper portion, toward the lower portion, translates the upper portion away from the lower portion, along the implant longitudinal axis, about a vertebral cut, to widen the vertebral cut, thereby expanding the spinal canal; and
each bulbous, swivelable coupling, tiltable relative to the implant longitudinal axis, during an entirety of the translation of the upper portion away from the lower portion along the implant longitudinal axis, angulates the entire inner member relative to the implant longitudinal axis, during an entirety of the translation, to accommodate a lateral offset of a vertebra occurring during the widening of the vertebral cut.

17. The implant of claim 16, wherein the upper and the lower portions are each cylindrically shaped, the inner bore of the upper portion is a longitudinally extending throughhole, the inner bore of the lower portion is a well, and movement of the bulbous, swivelable coupling of the upper portion is translated along the longitudinal axis toward the lower portion.

18. An implant for expanding a spinal canal, comprising:
an upper portion and a lower portion, each having an inner bore, wherein the upper portion is proximal to the lower portion, and wherein the upper portion includes a widened inner bore over a proximal portion thereof and a narrower inner bore over a distal portion thereof;
an inner member extending into the inner bore of, and interacting with, each of the upper and the lower portions;
one bulbous, swivelable coupling located in the inner bore of each of the upper and the lower portions, each bulbous, swivelable coupling communicating with a respective end of the inner member;
wherein: the inner bore of the upper portion defines an implant longitudinal axis;
each bulbous, swivelable coupling is rotatable and tiltable relative to the implant longitudinal axis;
the bulbous, swivelable coupling of the upper portion is free to translate along the implant longitudinal axis within the widened, proximal portion of the inner bore of the upper portion;
movement of the bulbous, swivelable coupling of the upper portion, within and relative to the widened, proximal portion of the inner bore of the upper portion, toward the lower portion, in a direction from a proximal end of the widened, proximal portion of the inner bore of the upper portion to and finally abutting against a distal end of the widened, proximal portion of the inner bore of the upper portion, to translate the upper portion away from the lower portion, along the implant longitudinal axis, about a vertebral cut, to widen the vertebral cut, thereby expanding the spinal canal; and
each bulbous, swivelable coupling, tiltable relative to the implant longitudinal axis, during translation of the upper portion away from the lower portion along the implant longitudinal axis, angulates the inner member relative to the implant longitudinal axis to accommodate a lateral offset of a vertebra occurring during the widening of the vertebral cut.

19. An implant for expanding a spinal canal, comprising:
an upper portion and a lower portion, each having an inner bore, wherein the upper portion is proximal to the lower portion, and wherein the upper portion includes a widened inner bore over a proximal portion thereof and a narrower inner bore over a distal portion thereof;
an inner member extending into the inner bore of, and interacting with, each of the upper and the lower portions;
one bulbous, swivelable coupling located in the inner bore of each of the upper and the lower portions, each bulbous, swivelable coupling communicating with a respective end of the inner member;
a retaining lock nut, threadably engaging inner walls of the widened, proximal portion of the inner bore of the upper portion;
wherein: the inner bore of the upper portion defines an implant longitudinal axis;
each bulbous, swivelable coupling is rotatable and tiltable relative to the implant longitudinal axis;
the bulbous, swivelable coupling of the upper portion is free to translate along the implant longitudinal axis within the widened, proximal portion of the inner bore of the upper portion;
movement of the bulbous, swivelable coupling of the upper portion, within and relative to the widened, proximal portion of the inner bore of the upper portion, toward the lower portion, translates the upper portion away from the lower portion, along the implant longitudinal axis, about a vertebral cut, to widen the vertebral cut, thereby expanding the spinal canal;
each bulbous, swivelable coupling, tiltable relative to the implant longitudinal axis, during translation of the upper portion away from the lower portion along the implant longitudinal axis, angulates the inner member relative to the implant longitudinal axis to accommodate a lateral offset of a vertebra occurring during the widening of the vertebral cut; and threadable advancement of the retaining lock nut moves the bulbous, swivelable coupling of the upper portion within the widened, proximal portion of the inner bore, secures the bulbous, swivelable coupling of the upper portion against a distal end of the widened, proximal portion of the inner bore, and secures the upper portion relative to the lower portion, after translation, about the vertebral cut, thereby securing and maintaining a width of the widened vertebral cut.

20. An implant for expanding a spinal canal, comprising:

an upper portion and a lower portion, each having an inner bore;

an inner member extending into the inner bore of, and interacting with, each of the upper and the lower portions, the inner member having an upper length and a lower length;

one swivelable coupling located within the inner bore of each of the upper and the lower portions, each swivelable coupling communicating with the inner member;

wherein: the inner bore of the upper portion defines an implant longitudinal axis;

the inner member includes external threads over at least a portion of the upper length thereof;

the swivelable coupling of the upper portion has a passage completely through the swivelable coupling, internally threaded over at least a portion thereof to accept the external threads of the upper length of the inner member, to threadably engage the upper length of the inner member, the inner member extending completely through the swivelable coupling;

the swivelable coupling of the lower portion, and the inner member, are retained, fixed from translation, within the lower portion;

threadable rotation about the implant longitudinal axis of the inner member relative to the swivelable coupling of the upper portion causes the inner member to translate the upper portion away from the lower portion, along the implant longitudinal axis, about a vertebral cut, to widen the vertebral cut, thereby expanding the spinal canal, and each swivelable coupling, tiltable relative to the implant longitudinal axis, during an entirety of the translation of the upper portion away from the lower portion along the implant longitudinal axis, angulates the entire inner member relative to the implant longitudinal axis, during an entirety of the translation, to accommodate a lateral offset of a vertebra occurring during the widening of the vertebral cut.

* * * * *